United States Patent [19]

Gurtzgen

[11] Patent Number: 5,446,001
[45] Date of Patent: Aug. 29, 1995

[54] PROCESS FOR THE PREPARATION OF ALKYLALUMINOXANES ON INERT SUPPORT MATERIALS

[75] Inventor: Stefan Gurtzgen, Wuppertal, Germany

[73] Assignee: Witco GmbH, Bergkamen, Germany

[21] Appl. No.: 213,946

[22] Filed: Mar. 16, 1994

[30] Foreign Application Priority Data

Oct. 27, 1993 [DE] Germany .................. 43 36 659.7

[51] Int. Cl.⁶ .............................................. C08F 4/44
[52] U.S. Cl. .................................. 502/151; 502/104; 502/152; 502/232
[58] Field of Search ................ 502/104, 151, 152, 232

[56] References Cited

U.S. PATENT DOCUMENTS

| | | | |
|---|---|---|---|
| 4,426,317 | 1/1984 | Rogers | 502/120 |
| 4,874,734 | 10/1989 | Kioka et al. | 502/104 |
| 4,904,631 | 2/1990 | Chang | 502/120 |
| 4,921,825 | 5/1990 | Kioka et al. | 502/104 |
| 4,937,217 | 6/1990 | Chang | 502/117 |
| 4,952,540 | 8/1990 | Kioka et al. | 502/152 |
| 5,026,797 | 6/1991 | Takahashi | 526/124 |
| 5,234,878 | 8/1993 | Tsutsui et al. | 502/103 |
| 5,308,816 | 5/1994 | Tsutsui et al. | 502/104 |

OTHER PUBLICATIONS

Kaminsky et al., *Polyhedron*, 7, 2375-2381 (1988).
Chien et al., *J. Polym. Science: Part A, Polym. Chem.*, 29, 1603-1607 (1991).

*Primary Examiner*—Sharon A. Gibson
*Assistant Examiner*—Walter D. Griffin
*Attorney, Agent, or Firm*—Scully, Scott, Murphy & Presser

[57] ABSTRACT

The invention relates to a process for the preparation of alkylaluminoxanes immobilized on inert support materials, characterized in that alkylaluminoxanes present in the form of dispersions are fixed on inert support materials.

20 Claims, 1 Drawing Sheet

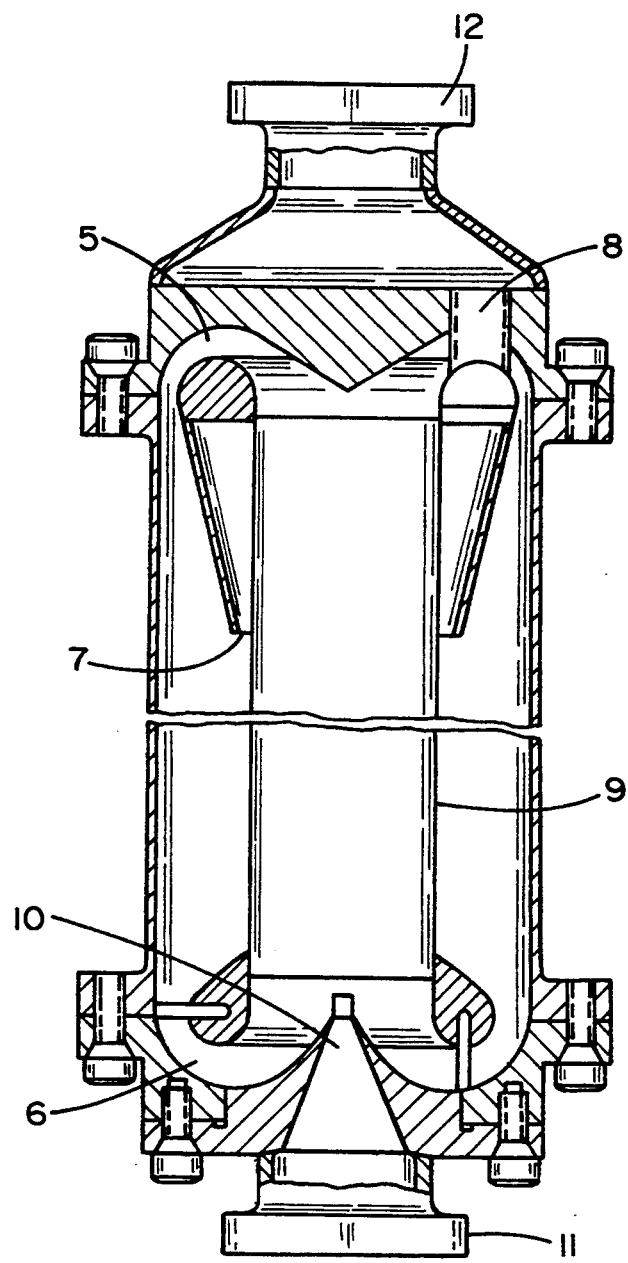

PROCESS FOR THE PREPARATION OF ALKYLALUMINOXANES ON INERT SUPPORT MATERIALS

BACKGROUND OF THE INVENTION

Alkylaluminoxanes, in particular methylaluminoxane, are becoming increasingly important as an essential component of a new generation of catalyst systems for the preparation of polyolefins ("single site catalysts"). These new catalysts consist essentially, as already known from classical Ziegler-Natta catalysts, of a transition metal compound as catalyst and the alkylaluminoxane mentioned at the beginning as organoaluminum cocatalyst component. The transition metal compounds used are preferably cyclopentadienyl, indenyl or fluorenyl derivatives of group IVa of the Periodic Table of the Elements. Unlike conventional Ziegler-Natta catalysts, such systems possess, in addition to high activity and productivity, not only the ability to give specific control of the product properties as a function of the components used and the reaction conditions, but furthermore provide access to hitherto unknown polymer structures with promising properties in respect of industrial applications.

In the literature there have been numerous publications which have the preparation of specific polyolefins with such catalyst systems as their subject. However, a disadvantage in practically all cases is the fact that in order to achieve acceptable productivities a large excess of alkylaluminoxanes, based on the transition metal component, is required (the ratio of aluminum in the form of the alkylaluminoxane to transition metal is customarily about 1000-cf. W. Kaminsky et al., Polyhedron, Vol. 7, No. 22/23 (1988) 2375 ff). Owing on the one hand to the high price of the alkylaluminoxanes and on the other hand to the additional polymer workup steps ("deashing steps") required in some cases, polymer production on an industrial scale based on such catalyst systems would in many cases be uneconomical. In addition, the toluene solvent frequently used for the formulation of alkylaluminoxanes, in particular methylaluminoxane, is increasingly undesirable for reasons of storage stability of the formulations (strong tendency towards gel formation) and also with respect to some applications of the polyolefins finally resulting.

A significant reduction in the amount of alkylaluminoxane required in relation to the transition metal component can be achieved by applying alkylaluminoxane to inert support materials, preferably $SiO_2$ (J. C. W. Chien, D. He, J. Polym. Science Part A, Polym. Chem., Vol. 29, 1603-1607 (1991). Such supported materials possess the further advantage of being able to be easily separated off in polymerizations in the condensed phase (preparation of highly pure polymers) or being able to be used as free-flowing powders in modern gas-phase processes, in which the particle morphology of the polymer can be determined directly by the particle shape of the support. Furthermore, dry powders of alkylaluminoxanes fixed on supports are physically more stable than solutions having a comparable aluminum content. This is the case particularly for methylaluminoxane which, as already mentioned, tends to form a gel in toluene solution after a certain storage time.

In the literature some ways have already been described for fixing alkylaluminoxanes on supports: EP 0 369 675 (Exxon Chemical) describes a process in which the immobilization of alkylaluminoxanes is achieved by reaction of an about 10% strength solution of trialkylaluminum in heptane with hydrated silica (8.7% by weight of $H_2O$).

In EP 0 442 725 (Mitsui Petrochemical), the immobilization is effected by reaction of a toluene/water emulsion with an about 7% strength solution of trialkylaluminum in toluene in the presence of silica at temperatures from $-50°$ C. to $+80°$ C.

A further alternative is provided by U.S. Pat. No. 5,026,797 (Mitsubishi Petrochemical), by reaction of ready-prepared alkylaluminoxane solutions with silica (pre-dried at 600° C.) at 60° C. and subsequent washing out of the non-immobilized proportion of alkylaluminoxane by means of toluene. Finally, U.S. Pat. No. 4,921,825 (Mitsui Petrochemical) describes a process for the immobilization of alkylaluminoxane by precipitation from toluene solutions by means of n-decane in the presence of silica.

These processes are in part technically complicated, since they comprise, inter alia, initially low reaction temperatures or multi-stage workup processes and losses in yield thus caused, or it is often not possible to achieve the degrees of loading of the support with alkylaluminoxanes required for high catalyst activity.

SUMMARY OF THE INVENTION

It was therefore an object of the present invention to overcome these disadvantages of the prior art and to provide a process by which alkylaluminoxanes can be fixed on inert support materials with high yield and homogeneity in a reproducible manner, in which the degrees of loading can be varied within wide limits, the particle morphology of the support is maintained and the products are finally obtained as free-flowing powders.

The invention provides a process for the preparation of alkylaluminoxanes, in particular methylaluminoxanes, immobilized on inert support materials, which process is characterized in that alkylaluminoxanes present in dispersed form, i.e. lyophilic dispersions in the form of a sol, (cf. Römpp Chemie Lexikon, 9th edition, Georg Thieme Verlag Stuttgart, New York 1990, p. 2299 ff) are fixed on inert support materials.

The invention further provides aluminoxanes fixed on support materials and prepared according to the process of the invention.

Further subjects of the invention are characterized by the claims.

BRIEF DESCRIPTION OF THE DRAWING

The FIGURE is a cross-sectional view of a jet loop reactor useful in carrying out the process of the present invention.

DETAILED DESCRIPTION OF THE INVENTION

The dispersions used according to the invention can be prepared by hydrolysis of alkylaluminum compounds in hydrocarbon solvents. The molar ratio of water to alkylaluminum compounds is here in the range from 0.8:1 to 1.3:1, preferably from 0.9:1 to 1.2:1.

According to the invention, preference is given to a preparative process in which water is metered into a solution of trialkylaluminum in an aliphatic, cycloaliphatic or preferably aromatic hydrocarbon solvent via a mixing nozzle into a static mixer, preferably a jet loop reactor (DE-A 43 14 986).

Suitable solvents are, in particular, aliphatic, cycloaliphatic or aromatic hydrocarbons such as pentane, hexane, heptane, octane, cyclohexane, methylcyclohexane and, in the case of the preparation of methylaluminoxane, preferably toluene and xylene.

The operation of the jet loop reactor, as it is described, for example, in DE-A-25 16 284, is based on a liquid propulsion jet in the internal tube, which imparts an impulse to the total reactor contents and thus produces a high circulating current. The liquid circulating flow in the reactor is therefore from about 8 to 10 times higher than the volume flow of the propulsion jet.

The flow in the reactor is in fact approximately as follows in referring to the Figure. The material to be mixed entering at the bottom center (11) of the reactor via the injection nozzle (10) is, by means of a bow-shaped configuration (5) at the upper end, made to flow back along the outer wall and, by means of a bow-shaped configuration (6) at the lower end, forced alongside the propulsion jet. On each further circulation, the recirculated liquid is mixed with the incoming liquid. A part of the liquid is flowing to the outer wall of the insert tube (9). Through the slot outlet (7) via the product exit opening (8) and and the product outlet (12) the liquid is flowing out of the reactor.

In the process of the invention, water is metered via the mixing nozzle into the jet loop reactor in a volume flow ratio of water: trialkylaluminum solution of 1:2,000 to 1:40,000, preferably 1:5,000–1:20,000.

As a result of the high circulation current, the jet loop reactor ensures good and extremely fast mixing of the alkylaluminum-containing solution with water. Owing to the high primary dispersal, it is possible to avoid a localized excessive concentration of water, which would otherwise cause losses in yield by formation of aluminum hydroxide on the one hand and an undesirably high proportion of unreacted trialkylaluminum on the other hand.

Furthermore, the average degree of oligomerization n, which is reflected in the average molecular weight of the reaction product, can be specifically influenced by appropriate metering in of the reactants and control of the reaction parameters. Thus, the molar ratio $H_2O$/-trialkylaluminum, particularly also in the case of trimethyl aluminum (TMA), can be set to the desired value, with a higher relative amount of water leading to a higher degree of oligomerization and leading hence to insolubility of the aluminoxane in the dispersion. This is of particular importance, since the activity of aluminoxanes as co-catalyst in olefin polymerization is evidently dependent on the degree of oligomerization of the aluminoxane used (references: W. Kaminsky, Nachr. Chem. Tech. Lab. 29, 373-7 (1981); W. Kaminsky et al., Makromol. Chem., Macromol. Symp. 3, 377-87 (1986)).

In principle, the organoaluminum compounds which can be used are any of the customary compounds in this field which can be hydrolyzed with water to give aluminoxanes. It is essential to the invention that a lyophilic dispersion of the compounds can be achieved in hydrocarbons. According to the invention, the hydrolysis products are lyophilic dispersions which occur in the sol state.

In the preparation of the aluminoxanes according to the invention, it is possible to use trialkylaluminum compounds of the formula $Al(R)_3$, where R is any alkyl radical having from 1 to 20 carbon atoms, such as ethyl, propyl, butyl, pentyl, octyl, 2-ethylhexyl and isopropyl radicals. Mixtures of two or more of these compounds may be used.

According to the invention, preference is given to trialkylaluminum compounds having short-chain alkyl radicals, in particular methyl radicals.

As support materials usable according to the invention, the porous oxides of one or more elements of groups II, III or IV of the Periodic Table such as $ZrO_2$, $TiO_2$, $B_2O_3$, CaO, ZnO, BaO, preferably $Al_2O_3$ and MgO and in particular $SiO_2$, are used.

These support materials can have particular sizes in the range of 1–300 microns, preferably 10–200 microns; surface areas of 10–1000 $m^2/g$, in particular 100–500 $m^2/g$; $N_2$ pore volumes of 0.5–3 $cm^3$, preferably 1–2 $cm^3$.

These supports are commercially available materials in which the indicated values are statistically distributed.

The water content of the support materials should be $\leq 5\%$ by weight, preferably $<3\%$ by weight and in particular $<1\%$ by weight. If necessary, the commercially available support materials are therefore dried before use at temperatures of 150°–1000° C., preferably 200°–500° C., for 2–20 hours, optionally at reduced pressure.

The application and fixing of the aluminoxanes to the support materials is carried out according to processes known per se either by continuous or batchwise addition of the support material to the previously prepared dispersions with simultaneous homogenization of the mixture, or by synthesis of the dispersions directly in the presence of the support. The solvent is then removed from these mixtures, under reduced pressure if necessary.

The original particle morphology of the support material is not altered by this procedure.

The ratio of support to aluminoxane can be varied within relatively wide limits; according to the invention the ratio is selected such that 5–40% by weight, and preferably 10–25% by weight, of aluminum are present in the form of aluminoxanes on the resulting free-flowing powder comprising support material and aluminoxane (see examples).

The process of the invention makes possible the preparation of supported aluminoxanes with virtually quantitative yields of immobilized aluminum, based on the trialkylaluminum compounds used, without technically complicated process steps. Due to the specifically adjustable parameters and reproducible process conditions, these supported alkylaluminoxanes, in particular the methylaluminoxane, prepared by the process of the invention have high activities as co-catalysts and are therefore exceptionally suitable for the further preparation of catalyst systems for olefin polymerization.

EXAMPLES

Example 1

A dispersion prepared with the aid of the jet loop reactor from 2.92 kg of trimethylaluminum (TMA) (aluminum content: 36.8%), 0.58 kg of water and 21.5 kg of toluene (molar ratio $H_2O/TMA = 0.8$) was mixed by stirring with 2.0 kg of silica support material (surface area ($N_2$-BET): 316 $m^2/g$; $N_2$-pore volume: 1.55 ml/g; particle size distribution: 20–80 microns; residual water content: 2.6%) in a 40 l steel reactor and evaporated to dryness in vacuo at room temperature. 4.3 kg of supported methyl aluminoxane (MAO) were obtained in the form of a free-flowing powder (aluminum content: 24.5%=98% of theory based on aluminum used; ratio methyl/aluminum: 1.2). 3 hours' extraction with toluene at 90° C. and subsequent analysis of the toluene phase showed that complete immobilization had been achieved.

Example 2

Using the procedure of Example 1, a dispersion prepared from 1.29 kg of TMA, 0.29 kg of water and 10.5 kg of toluene (molar ratio $H_2O$/TMA=0.9) was mixed by stirring with 3.5 kg of silica (residual water content: 0.3%) and evaporated to dryness in vacuo. 4.6 kg of free-flowing powder were obtained (aluminum content: 10.0%=97% of theory; methyl/aluminum: 1.2), with complete immobilization being able to be shown analogously to Example 1.

What is claimed is:

1. A process for the preparation of an alkylaluminoxane immobilized on an inert support material comprising hydrolyzing at least one trialkylaluminum compound dissolved in a hydrocarbon solvent by metering said water into a jet loop reactor, such that the volume flow ratio of said water to said trialkylaluminum solution is in the range of between 1:2,000 and 1:40,000 to provide a molar ratio of said water to said trialkylaluminum compound in the range of between 0.8:1 and 1.3:1, whereby an alkylaluminoxane lyophilic dispersion is formed; and contacting said dispersion with an inert support material.

2. A process in accordance with claim 1 wherein said molar ratio of said water to said trialkylaluminum compound is in the range of between 0.9:1 and 1.2:1.

3. A process in accordance with claim 2 wherein said volume flow ratio of said water to said trialkylaluminum solution is in the range of between 1:5,000 and 1:20,000.

4. A process in accordance with claim 1 wherein said hydrocarbon solvent is an aromatic hydrocarbon.

5. A process in accordance with claim 4 wherein said aromatic hydrocarbon is selected from the group consisting of toluene and xylene.

6. A process in accordance with claim 1 wherein said trialkylaluminum compound is trimethylaluminum.

7. A process in accordance with claim 7 wherein said alkylaluminoxane is methylaluminoxane.

8. A process in accordance with claim 1 wherein said inert support has a particle size range of 1 to 300 microns, a surface area of 10 to 1,000 square meters per gram and a pore volume of 0.5 to 3 $cm^3$.

9. A process in accordance with claim 8 wherein said inert support is silica having a water content of less than 5% by weight.

10. A process in accordance with claim 9 wherein said silica has a water content of less than 3% by weight.

11. A process in accordance with claim 1 including the step of removing the solvent subsequent to contacting said alkylaluminoxane dispersion with said inert support material.

12. A process in accordance with claim 11 wherein said step of removing said solvent results in a product which comprises between 5% and 40% by weight of aluminum, based on the total weight of said alkylaluminoxane and said support material.

13. A process in accordance with claim 12 wherein said aluminum comprises between 10% and 25% by weight of the total weight of said alkylaluminoxane and said support material.

14. A process in accordance with claim 1 wherein said step of contacting said dispersion with said support material comprises metering of said support material into said dispersion.

15. A process in accordance with claim 1 wherein said step of contacting said dispersion with said inert support material comprises including said support material in said loop jet reactor during said hydrolyzation step.

16. A process for the preparation of methylaluminoxane immobilized on silica comprising hydrolyzing a solution of trimethylaluminum in toluene with water by metering said water into a jet loop reactor such that the volume flow rate of said water to said trimethylaluminum solution is in the range of between 1:2,000 and 1:40,000 to provide a molar ratio of said water to said trimethylaluminum in the range of between 0.8:1 and 1.3:1 whereby a lyophilic dispersion of methylaluminoxane is formed; contacting said dispersion with silica; and driving off said toluene to produce a free flowing powder.

17. A process in accordance with claim 16 wherein said volume flow rate of water to trimethylaluminum solution is in the range of between 1:5,000 and 1:20,000.

18. A process in accordance with claim 17 wherein said silica has a water content of less than 3% by weight and is characterized by a particle size range of between 10 and 200 microns, a surface area of 100 to 500 square meters per gram and a pore volume of 1 to 2 $cm^3$.

19. A product comprising an alkylaluminoxane immobilized on an inert support prepared in accordance with the process of claim 1.

20. A product comprising methylaluminoxane immobilized on silica prepared in accordance with the process of claim 16.

* * * * *